United States Patent [19]

Ohno et al.

[11] Patent Number: 5,739,177
[45] Date of Patent: Apr. 14, 1998

[54] DENTAL COMPOSITION

[75] Inventors: Hideki Ohno; Mikio Kimura; Satoru Fuchigami; Makoto Oguri, all of Tokuyama, Japan

[73] Assignee: Tokuyama Corporation, Tokuyama, Japan

[21] Appl. No.: 659,621

[22] Filed: Jun. 6, 1996

Related U.S. Application Data

[63] Continuation of Ser. No. 364,093, Dec. 27, 1994, abandoned.

[30] Foreign Application Priority Data

Dec. 28, 1993 [JP] Japan ............................ 5-336957

[51] Int. Cl.$^6$ ............................................. A61K 6/08
[52] U.S. Cl. ........................... 523/118; 523/116; 522/27; 524/157; 524/158; 524/167; 524/300; 524/319; 526/277; 526/278; 526/318; 526/318.42
[58] Field of Search ........................ 524/157, 158, 524/167, 300, 319; 523/116, 118; 522/27; 526/277, 278, 318.42, 318

[56] References Cited

U.S. PATENT DOCUMENTS

| | | | |
|---|---|---|---|
| 4,964,911 | 10/1990 | Ibsen et al. | 523/118 |
| 5,204,383 | 4/1993 | Manabe et al. | 523/118 |
| 5,270,351 | 12/1993 | Bowen | 523/116 |
| 5,338,773 | 8/1994 | Lu et al. | 523/118 |

FOREIGN PATENT DOCUMENTS

| | | |
|---|---|---|
| 0206810 | 12/1986 | European Pat. Off. . |
| 0305083 | 3/1989 | European Pat. Off. . |
| 0408357 | 1/1991 | European Pat. Off. . |

OTHER PUBLICATIONS

Patent Abstracts of Japan, vol. 18, No. 542 (C–1261), Oct. 17, 1994 Abstract of Japanese Laid–Open Application No. 6-192030 (Jul. 12, 1994).

Database WPI, Section Ch, Week 8532, Derwent Publ., Ltd., London, U.K. Abstract of Japanese Laid–Open Application No. 6-123,515 (Jul. 2, 1985).

*Primary Examiner*—Andrew E. C. Merriam
*Attorney, Agent, or Firm*—Sherman and Shalloway

[57] ABSTRACT

A dental composition containing an acid such as maleic acid, phosphoric acid or citric acid; an organosulfonate and/or an organosulfinate such as an acid group-containing (meth) acrylate monomer having in the molecules thereof a carboxyl group or a phosphoric acid group, a sodium benzenesulfonate or a sodium p-toluenesulfinate; a water-soluble organic solvent such as ethanol or propanol; and the water: but without substantially containing any polymerizable monomer except the above acid group-containing (meth) acrylate monomer, or further containing a hydroxy- or a dihydroxyalkyl (meth)acrylate monomer. For adhesion of a dental filling material to teeth, the composition of the invention is used as a pre-treatment agent on teeth prior to applying an adhesive. This makes it possible to treat enamel and dentin simultaneously and to accomplish strong adhesive strength to both of them. The composition does not excessively remove smear plugs in the dentin after it is treated, and external stimulation is less probable to reach the dental pulp.

6 Claims, No Drawings

DENTAL COMPOSITION

This application is a continuation of application Ser. No. 08/364,093, filed Dec. 27, 1994, now abandoned.

DETAILED DESCRIPTION OF THE INVENTION

1. (Field of the Invention)

The present invention relates to a dental composition that is suited for use as a pre-treatment agent for accomplishing a high adhesive strength between a dental filling material and a tooth at the time of restoring the tooth in the field of dental treatment.

2. (Prior Art)

Dental filling materials called composite resins are mainly used for repairing teeth that are damaged by dental caries. Generally, the composite resin is filled in a cavity of a tooth and is then polymerized and cured. However, this material has no adhesiveness to the tooth and, hence, a dental adhesive is used in combination. The adhesive should have adhesive strength that is large enough to overcome the internal stress that generates when the composite resin cures, i.e., large enough to overcome the tensile strength that generates at an interface between the composite resin and the tooth. Otherwise, the composite resin may fall off after used for extended periods of time, or form a gap at the interface between the composite resin and the tooth permitting the infiltration of bacteria that adversely affect dental pulp.

Because the hard tissue of a tooth consists of enamel and dentin, the adhesive should have adhesiveness to both of them. In order to improve adhesiveness, so far, a method has heretofore been employed according to which the surface of a tooth is pre-treated prior to applying the adhesive. As a material for effecting the pre-treatment, an acid-containing aqueous solution is generally used to decalcify the surface of the tooth, such as an aqueous solution containing phosphoric acid, citric acid, maleic acid or the like acid. In the case of the enamel, it is said that the adhesion mechanism to the treated surface is a macroscopic mechanical retention in which the adhesive infiltrates into, and cures in, the coarse surface created by decalcification with an acid-containing aqueous solution. In the case of the dentin, it is said that the adhesion mechanism is a microscopic mechanical retention in which the adhesive infiltrates into, and cures in, fine openings of collagen fiber network exposed on the surface of the tooth after decalcification. However, because the adhesive does not infiltrate into collagen fiber so easily as into the enamel surface, an infiltration promoting agent called primer is usually applied after decalcification. However, this procedure makes the operation cumbersome. In order to simplify the operation, Japanese Laid-Open Patent Publication No. 123515/1985 is disclosing a pre-treatment composition comprising an unsaturated carboxylic acid, a (meth)acrylic ester monomer and an organosulfinate. However, even this composition does not realize sufficient adhesive strength to the tooth.

There further arouses another problem in that when the enamel and the dentin are simultaneously treated with above-mentioned acid-containing aqueous solution that is generally used, the enamel should be strongly decalcified to obtain a sufficient adhesive strength causing, however, dentin to be subjected to excess decalcification. That is, chips called smear intimately adhere on the surface of the dentin that is ground for the purpose of forming a dental cavity and form a smear layer thereon. The smear infiltrates from the surface of the dentin into dentinal tubules communicating to the dental pulp, causing the tubules to be clogged with plugs called smear plugs. However, the excess degree of decalcification removes the smear plugs so that the permeation through the tubules in the dentin increases (Shinkai, Kato, Journal of 35(3), 634, 1992) arousing, however, a problem in that harmful substances easily infiltrate into the dental pulp through the tubules. In recent years the idea that excess decalcification damages dentin that is a vital tissue is becoming widely accepted. Therefore, it is desired to suppress the decalcification of dentin as small as possible.

In the art of restoring dental cavity by effecting the pre-treatment, applying an adhesive and filling a composite resin under the above-mentioned circumstances, it has been desired to develop a material that can be used as a pre-treatment material without requiring cumbersome operation of applying a primer, that exhibits high adhesive strength to both the enamel and the dentin, and that decalcifies the dentin to a suitable degree leaving smear plugs.

The present inventors have conducted keen study in an effort to overcome the above-mentioned technical assignments and have found the fact that a composition comprising an acid, an acid group-containing (meth)acrylate monomer, an organosulfonate and/or an organosulfinate, a water-soluble organic solvent and the water, can be used as a pre-treatment agent that exhibits a high adhesive strength to the enamel and to dentin without any primer, leaving a suitable degree of smear plugs in dentin.

The inventors have further found the fact that a composition comprising an acid, an acid group-containing (meth)acrylate monomer, an organosulfonate and/or an organosulfinate, a water-soluble organic solvent, the water and a hydroxy- or a dihydroxy(meth)acrylate monomer, can be used as a pre-treatment agent that exhibits a high adhesion strength to enamel and to dentin without any primer, leaving a suitable degree of smear plugs in the dentin.

The present application encompasses two inventions, wherein a first invention is concerned with a dental composition comprising (A) an acid having an acid dissociation constant (hereinafter abbreviated as pKa) of not larger than 4, (B) an acid group-containing (meth)acrylate monomer, (C) an organosulfonate and/or an organosulfinate, (D) a water-soluble organic solvent, and (E) the water, wherein a blending amount of (A) is from 5 to 200 mmol with respect to the total amount of 100 g of (B), (C), (D) and (E), and blending amounts of (B), (C), (D) and (E) are from 1 to 30 parts by weight, 1 to 20 parts by weight, 10 to 90 parts by weight, and 5 to 80 parts by weight, respectively, with respect to the total amount of 100 parts by weight of (B), (C), (D) and (E).

A second invention is concerned with a dental composition comprising (A) an acid having an acid dissociation constant (hereinafter abbreviated as pKa) of not larger than 4, (B) an acid group-containing (meth)acrylate monomer, (C) an organosulfonate and/or an organosulfinate, (D) a water-soluble organic solvent, (E) the water, and (F) a hydroxy- or a dihydroxy(meth)acrylate monomer, wherein a blending amount of (A) is from 5 to 200 mmol with respect to the total amount of 100 g of (B), (C), (D), (E) and (F), and blending amounts of (B), (C), (D), (E) and (F) are from 1 to 30 parts by weight, 1 to 20 parts by weight, 10 to 90 parts by weight, 5 to 80 parts by weight, and 1 to 40 parts by weight, respectively, with respect to the total amount of 100 parts by weight of (B), (C), (D), (E) and (F).

There is no particular limitation upon the acid that is used in the present invention provided its pKa is not larger than 4, and any known inorganic acid or organic acid can be used. When pKa exceeds 4, it becomes difficult to decalcify the tooth to a sufficient degree, and practicable adhesive strength is not obtained. The pKa of a polybasic acid is calculated from a dissociation constant in a first stage.

Examples of the inorganic acid that can be used in the present invention include nitric acid, phosphoric acid, hydrochloric acid and sulfuric acid. Among them, nitric acid and phosphoric acid can be preferably used. As the organic acid, there can be used monocarboxylic acid, dicarboxylic acid, tricarboxylic acid or tetracarboxylic acid. Examples of the monocarboxylic acid include formic acid, lactic acid, pyruvic acid, glycolic acid, chloroacetic acid, dichloroacetic acid, trichloroacetic acid, cyanoacetic acid and the like. Examples of the dicarboxylic acid include tartaric acid, succinic acid, glutaric acid, maleic acid, fumaric acid, malonic acid, citraconic acid, (o, m, p) phthalic acids and the like. Examples of the tricarboxylic acid include citric acid, tricarballylic acid, 1,3,5-pentanetricarboxylic acid, trimellitic acid and the like. As desired, furthermore, a plurality of acids may be selected from the above-mentioned inorganic acids or the organic acids, and may be used being mixed together.

Among the above-mentioned acids, it is desired to use an organocarboxylic acid having an acid dissociation constant of not larger than 3 from the standpoint of adhesion to teeth and stimulation to dental pulp.

According to the first invention, the above-mentioned acid is blended in an amount of from 10 to 200 mmol and, preferably, from 15 to 150 mmol with respect to the total amount of 100 g of an acid group-containing (meth)acrylate monomer, an organosulfonate and/or an organosulfinate, a water-soluble organic solvent and the water. According to the second invention, the above-mentioned acid is blended in an amount of from 10 to 200 mmol and, preferably, from 15 to 150 mmol with respect to the total amount of 100 g of an acid group-containing (meth)acrylate monomer, an organosulfonate and/or an organosulfinate, a water-soluble organic solvent, the water and a hydroxy- or a dihydroxy (meth)acrylate monomer.

When the blending amount is larger than the above-mentioned range, smear plugs are completely removed. When the blending amount is smaller than the above-mentioned range, on the other hand, the enamel is not decalcified sufficiently. Among the aforementioned acids that are usually used in the form of an aqueous solution, the water in the aqueous solution is calculated as one of the components of the present invention as will be described later.

As the acid group-containing (meth)acrylate monomer of the present invention, there can be used any known compound provided it has a carboxyl group or an anhydride thereof, or an acid group such as phosphoric acid group in the molecules thereof. A representative example of the acid group-containing (meth)acrylate monomer is expressed by the following general formula,

$$m = 1-4 \quad n = 1,2$$

wherein $R_1$ is a hydrogen atom or a methyl group, $R_2$ is an organic residue having a valency of 2 to 6 and 1 to 20 carbon atoms, which may further have ether group and/or ester group, and X is a group containing carboxyl group, anhydrous carboxyl group, phosphoric acid group or phosphoric ester group.

In the above general formula, X is a group containing carboxyl group, anhydrous carboxyl group, phosphoric acid group or phosphoric ester group, and though there is no particular limitation on the structure thereof, its preferred examples are as described below.

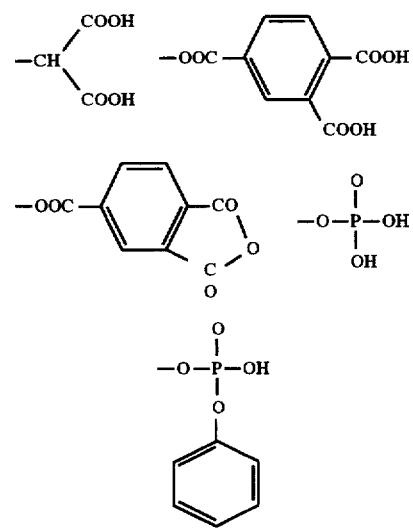

In the above-mentioned general formula, through there is no particular limitation on the structure, the organic residue $R_2$ has a valency of 2 to 6 and 1 to 20 carbon atoms and further has known ether group and/or ester group. Its concrete examples are as described below.

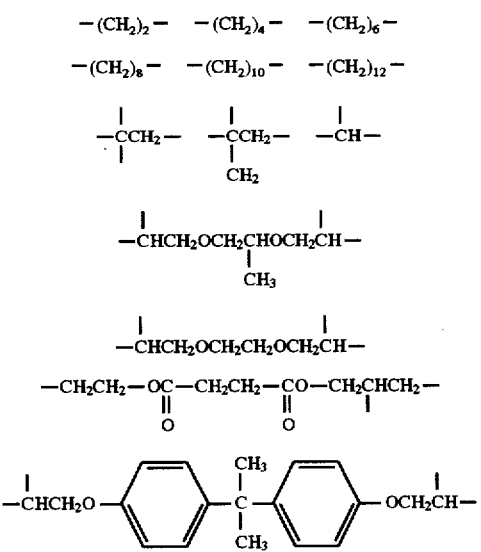

Preferred examples of the acid group-containing (meth) acrylate monomer expressed by the above-mentioned general formula are described below.

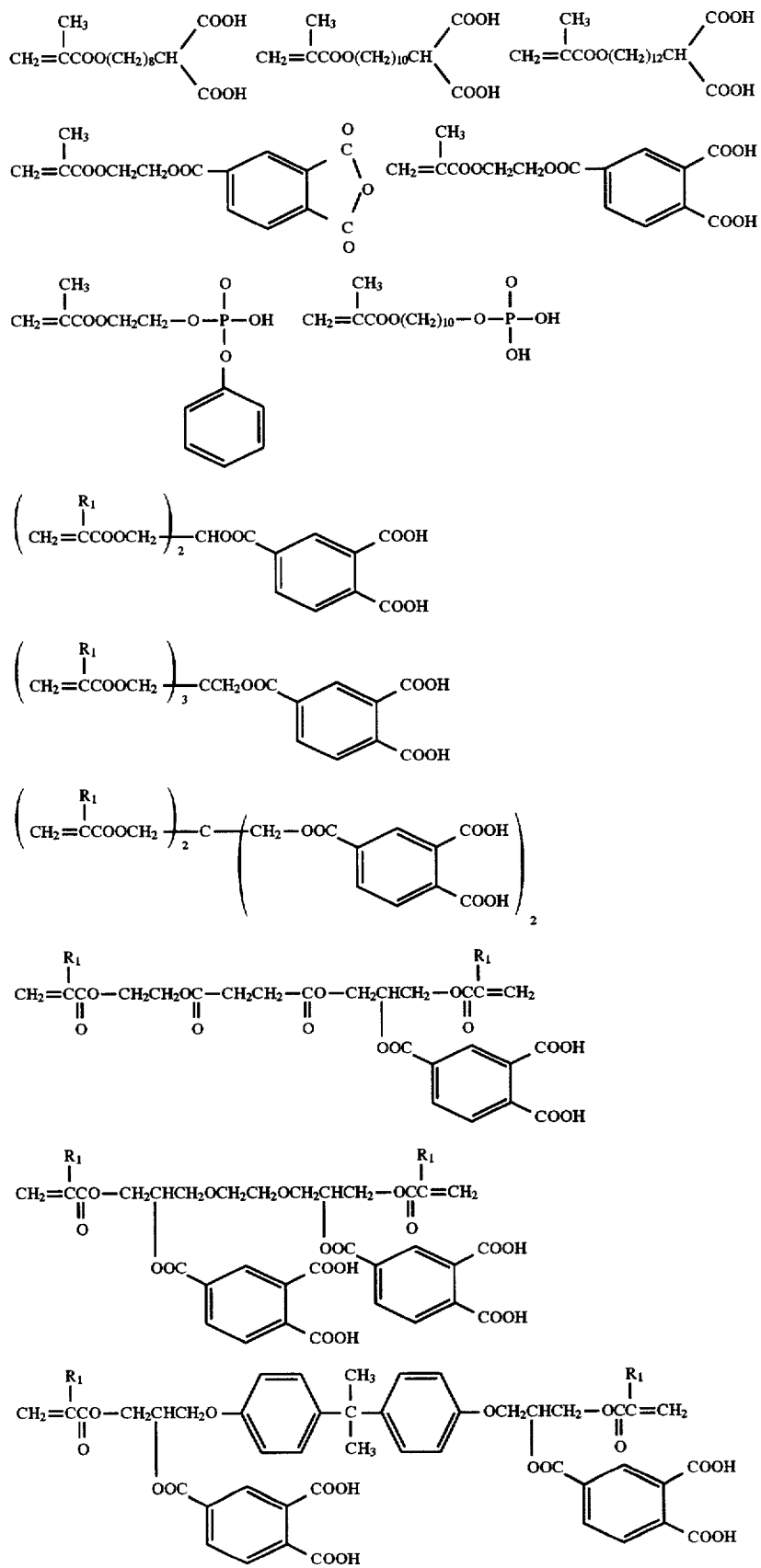

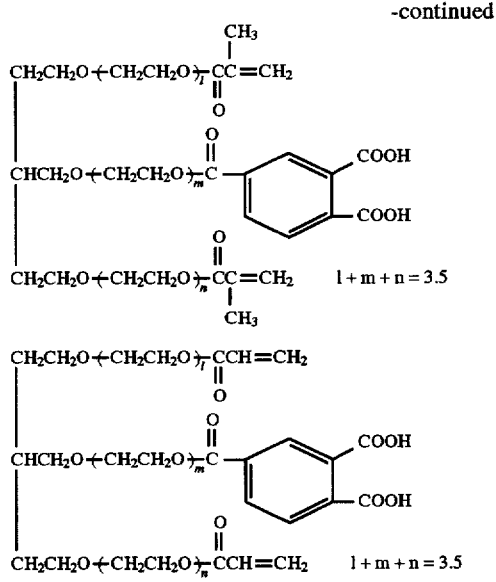

wherein $R_1$ is a hydrogen atom or a methyl group.

From the standpoint of adhesion to teeth, those having a carboxyl group or an anhydrous carboxyl group are particularly preferably used among the acid group-containing (meth)acrylate monomers that are concretely described above.

According to the first invention, the acid group-containing (meth)acrylate monomer is blended in an amount of from 1 to 30 parts by weight and, preferably, from 2 to 20 parts by weight with respect to the total amount of 100 parts by weight of the acid group-containing (meth)acrylate monomer, organosulfonate and/or organosulfinate, water-soluble organic solvent and water. According to the second invention, the acid group-containing (meth)acrylate monomer is blended in an amount of from 1 to 30 parts by weight and, preferably, from 2 to 20 parts by weight with respect to the total amount of 100 parts by weight of the acid group-containing (meth)acrylate monomer, organosulfonate and/or organosulfinate, water-soluble organic solvent, water and hydroxy- or dihydroxy(meth)acrylate monomer.

According to the first invention, addition of a polymerizable (meth)acrylate monomer other than the above-mentioned acid group-containing (meth)acrylate monomer should be avoided as it may deteriorate adhesion to the tooth. However, the hydroxy- or dihydroxy (meth)acrylate monomer helps increase the adhesion to both dentin and enamel when it is used in combination with the acid group-containing (meth)acrylate monomer.

Examples of the polymerizable (meth)acrylate monomer that should not be used include the following monomers; i.e., monofunctional monomers such as methyl methacrylate, ethyl methacrylate, tetrahydrofurfuryl methacrylate and acrylates thereof; aromatic bifunctional monomers such as 2,2-bis(4-methacryloyloxyethoxyphenyl) propane,
2,2-bis(4-methacryloyloxydiethoxyphenyl) propane,
2,2-bis(4-methacryloyloxytetraethoxyphenyl) propane,
2,2-bis(4-methacryloyloxypentaethoxyphenyl) propane,
2,2-bis(4-methacryloyloxydipropoxyphenyl) propane,
2(4-methacryloyloxyethoxyphenyl)-2(4-methacryloyloxydiethoxyphenyl) propane,
2(4-methacryloyloxydiethoxyphenyl)-2(4-methacryloyloxytriethoxyphenyl) propane,
2(4-methacryloyloxydipropoxyphenyl)-2(4-methacryloyloxytriethoxyphenyl) propane,
2,2-bis(4-methacryloyloxydipropoxyphenyl) propane,
2,2-bis(4-methacryloyloxyisopropoxyphenyl) propane and acrylates thereof; aliphatic bifunctional monomers such as ethylene glycol dimethacrylate, diethylene glycol dimethacrylate, triethylene glycol dimethacrylate, butylene glycol dimethacrylate, neopentyl glycol dimethacrylate, propylene glycol dimethacrylate, 1,3-butanediol dimethacrylate, 1,4-butanediol dimethacrylate, 1,6-hexanediol dimethacrylate and acrylates thereof; trifunctional monomers such as trimethylolpropane trimethacrylate, trimethylolethane trimethacrylate, trimethylolpropane trimethacrylate and acrylates thereof; and tetrafunctional monomers such as pentaerythritol tetramethacrylate, pentaerythritol tetraacrylate and the like.

As the organosulfonate and/or organosulfinate that is used in the present invention, any known salts of organosulfonic acid or organosulfinic acid can be used without any particular limitation.

Examples of the organosulfonic acid that forms the organosulfonate include alkylsulfonic acids such as methanesulfonic acid, ethanesulfonic acid, and n-hexanesulfonic acid; aromatic sulfonic acids such as benzenesulfonic acid, o-toluenesulfonic acid, p-toluenesulfonic acid, ethylbenzenesulfonic acid, 4-aminobenzenesulfonic acid, 2-amino-5-methylbenzene-1-sulfonic acid, p-phenylsulfonic acid, decylbenzenesulfonic acid, dodecylbenzenesulfonic acid, and chlorobenzenesulfonic acid; and vinylsulfonic acids such as methallylsulfonic acid and p-methacryloxysulfonic acid. Among these organosulfonic acids, an aromatic sulfonic acid is desirably used from the standpoint of adhesion strength to the dentin.

Examples of the organosulfinic acid that forms the organosulfinate include alkylsulfinic acids such as methanesulfinic acid, ethanesulfinic acid and n-hexanesulfinic acid; and aromatic sulfinic acids such as benzenesulfinic acid, o-toluenesulfinic acid, p-toluenesulfinic acid, ethylbenzenesulfinic acid, decylbenzenesulfinic acid, dodecylbenzenesulfinic acid and chlorobenzenesulfinic acid. Among these organosulfinic acids, an aromatic sulfinic acid is desirably used from the standpoint of adhesive strength to teeth.

Examples of the cation that forms a salt with the above-mentioned organosulfonic acid or organosulfinic acid include alkali metals such as lithium, sodium and potassium; alkaline earth metals such as magnesium, calcium, strontium and barium; ammonium compounds such as ammonium, tetramethyl ammonium, tetraethyl ammonium, tetrapropyl ammonium and trimethylbenzyl ammonium; and amines such as methylamine, ethylamine, propylamine, butylamine, aniline, toluidine, phenylenediamine, piperidine, N-methylaniline, N-ethylaniline, diphenylamine, N-methyltoluidine, trimethylamine, triethylamine, N,N-dimethylaniline, pyridine, N,N-diethylaniline, N,N-dimethyltoluidine and the like.

The most preferred examples of the organosulfonate and/or organosulfinate include sodium p-toluene sulfonate, sodium benzene sulfonate, sodium dodecylbenzene sulfonate, sodium p-toluene sulfinate, lithium p-toluene sulfinate, sodium benzene sulfinate and lithium benzene sulfinate.

According to the first invention, the organosulfonate and/or organosulfinate is added in an amount of from 1 to 20 parts by weight with respect to the total amount of 100 parts by weight of the acid group-containing (meth)acrylate monomer, organosulfonate and/or organosulfinate, water-soluble organic solvent and water. According to the second invention, the organosulfonate and/or organosulfinate is added in an amount of from 1 to 20 parts by weight with respect to the total amount of 100 parts by weight of the acid group-containing (meth)acrylate monomer, organosulfonate and/or organosulfinate, water-soluble organic solvent, water and hydroxy- or dihydroxy(meth)acrylate monomer.

In the present invention, the organosulfonate and the organosulfinate contribute to increasing the adhesive strength to teeth. Though the mechanism of action is not yet clear, it is presumed that they contribute to enhancing polymerization of the pre-treatment agent and of the adhesive at the interface of teeth.

According to the present invention, the water-soluble organic solvent is necessary for homogeneously dissolving other components. Its concrete examples include alcohols and ethers such as methanol, ethanol, propanol, butanol, ethylene glycol, propanediol, butanediol, pentanediol, butenediol, glycerin, trimethylolpropane, hexanetriol, allyl alcohol, diethylene glycol, diethylene glycol monomethyl ether, diethylene glycol monoethyl ether, triethylene glycol, triethylene glycol monomethyl ether, tetraethylene glycol, propylene glycol, dipropylene glycol, tripropylene glycol, 2-methoxyethanol, 2-ethoxyethanol, 2-(methoxyethoxy)ethanol, 2-isopropoxyethanol, 2-butoxyethanol, 1-methoxy-2-propanol, 1-ethoxy-2-propanol, dipropylene glycol, dipropylene glycol monomethyl ether, tripropylene glycol monomethyl ether, glycerine ether and the like, as well as ketones such as acetone, methyl ethyl ketone and the like.

Among them, it is desired to use those that are little harmful to the living body, such as ethanol, propanol, ethylene glycol, propanediol, butanediol, pentanediol, glycerine, trimethylolpropane, hexanetriol, allyl alcohol, diethylene glycol, diethylene glycol monomethyl ether, diethylene glycol monoethyl ether, triethylene glycol, triethylene glycol monomethyl ether, tetraethylene glycol, propylene glycol, dipropylene glycol, tripropylene glycol, dipropylene glycol, dipropylene glycol monomethyl ether, tripropylene glycol monomethyl ether, glycerine ether, acetone and the like. Most desirably, use is made of alcohols such as ethanol, propanol, ethylene glycol, propanediol and the like.

As required, two or more water-soluble solvents may be used being mixed together. When the above-mentioned alcohols are to be used being mixed together with other water-soluble organic solvent, however, it is desired that the alcohols are added in an amount of not smaller than 30 parts by weight and, preferably, not smaller than 50 parts by weight with respect to the whole amount of the water-soluble organic solvent from the standpoint of forming a uniform film of the acid group-containing (meth)acrylate monomer and increasing the adhesive strength to teeth as will be described later.

According to the first invention, the water-soluble organic solvent is added in an amount of from 10 to 90 parts by weight with respect to the total amount of 100 parts by weight of the acid group-containing (meth)acrylate monomer, organosulfonate and/or organosulfinate, water-soluble organic solvent and water. According to the second invention, the water-soluble organic solvent is added in an amount of from 10 to 90 parts by weight with respect to the total amount of 100 parts by weight of the acid group-containing (meth)acrylate monomer, organosulfonate and/or organosulfinate, water-soluble organic solvent, water and hydroxy or dihydroxy (meth)acrylate.

According to the present invention, the water is necessary for decalcifying teeth. It is desired that the water does not substantially contain impurities that are detrimental to preservation stability, biocompatibility and adhesive property. Preferred examples include deionized water and distilled water.

According to the first invention, the water is added in an amount of from 5 to 80 parts by weight with respect to the total amount of 100 parts by weight of the acid group-containing (meth)acrylate monomer, organosulfonate and/or organosulfinate, water-soluble organic solvent and water. According to the second invention, the water is added in an amount of from 5 to 80 parts by weight with respect to the total amount of of 100 parts by weight of the acid group-containing (meth)acrylate monomer, organosulfonate and/or organosulfinate, water-soluble organic solvent, water and hydroxy or dihydroxy (meth)acrylate.

The hydroxy or dihydroxyalkyl (meth)acrylate monomer used in the second invention helps further increase of adhesiveness to the tooth when it is used together with an acid group-containing (meth)acrylate monomer. Examples of this monomer include hydroxyethyl (meth)acrylate, hydroxypropyl (meth)acrylate, glyceryl mono(meth)acrylate, glyceryl di(meth)acrylate and the like. Preferably, however, there is used a monoester of a polyhydric alcohol with not more than 3 carbon atoms and a (meth)acrylic acid.

The hydroxy or dihydroxy(meth)acrylate monomer is added in an amount of from 1 to 40 parts by weight and, preferably, from 3 to 30 parts by weight with respect to the total amount of 100 parts by weight of the acid group-containing (meth)acrylate monomer, organosulfonate and/or organosulfinate, water-soluble organic solvent, water and hydroxy or dihydroxy(meth)acrylate monomer.

The composition of the present invention can be blended with a water-insoluble organic solvent and a viscosity-increasing agent in such small amounts as will not impair properties of the composition. Examples of the water-insoluble organic solvent will be hexane, heptane, octane, toluene, dichloromethane, chloroform, carbon tetrachloride, dichloroethane, trichloroethane, methyl ethyl ketone, pantanone, hexanone, ethyl formate, propyl formate, butyl formate, ethyl acetate, propyl acetate and butyl acetate. Examples of the viscosity-increasing agent include high molecular compounds such as polyvinyl pyrrolidone, carboxymethyl cellulose, polyvinyl alcohol and the like, as well as highly dispersing silica. Moreover, edible coloring matters may be blended as coloring materials.

There is no particular limitation on a process for preparing the composition of the present invention. The aforementioned acid, acid group-containing (meth)acrylate monomer, organosulfonate, organosulfinate, water and hydroxy-or dihydroxy(meth)acrylate monomer can be weighed at predetermined ratios, introduced into a container, and are stirred and mixed together until they are homogenized.

The dental composition of the present invention is used as a pre-treatment agent in the art of restoring a tooth by applying the pre-treatment agent to the tooth surfaces, washing the tooth with the water, drying the tooth, applying an adhesive to the tooth, curing the adhesive, packing a filling material, and curing the filling material. In order to obtain a favorable adhesive strength in this case, it has been confirmed that a film of an acid group-containing (meth) acrylate monomer should have been uniformly formed on the surface of the tooth after the pre-treatment agent is washed with the water. If the mechanism of adhesion is so postulated that a layer that contributes to adhesion is formed through diffusion of the applied adhesive component into the film of the acid group-containing (meth)acrylate monomer, then it can be presumed that formation of a uniform film is a prerequisite for forming the adhesive layer.

The manner of packaging the composition of the present invention can be suitably determined provided it does not impair the preservation stability. For instance, a solution of an organosulfonate and/or an organosulfinate and water, and another solution of an acid having pKa of not larger than 4, an acid group-containing (meth)acrylate monomer and a water-soluble organic solvent, are separately packaged, and are mixed together when they are to be used.

In order to use the composition of the present invention, however, all of the components must be mixed and treated simultaneously. For instance, a sufficiently large adhesion strength to the tooth is not obtained even when the tooth surface is decalcified with a solution of an acid having pKa of not larger than 4, an acid group-containing (meth)acrylate monomer and a water-soluble organic solvent, and is washed with the water, dried and then a solution of an organosulfonate and/or an organosulfinate and water is applied thereto. Though the reason is not clear, it is considered that the acid group-containing (meth)acrylate monomer that is present in the step of decalcification the tooth infiltrates into the surface of the tooth.

For adhesion of the filling material to the tooth with an adhesive, pre-treating the surface of the tooth using the composition of the present invention makes it possible to treat enamel and dentin simultaneously and besides permitting them to be highly strongly adhered together. Furthermore, smear plugs that are formed during cavity preparation and fill dentinal tubes are not excessively removed, and external stimulation is little probable to arrive at the dental pulp, which is a safer adhesion to the living body.

EXAMPLES

The composition of the present invention will now be concretely described by way of Examples to which only, however, the invention is in no way limited. Here, properties of the materials mentioned in the specification and Examples are measured as described below.

(1) Adhesive Strength to the Enamel and Dentin

A camphorquinone and an ethyl p-dimethylaminobenzoate ester were dissolved each in an amount of 0.2 g in 6 g of a bis-GMA, 21 g of a triethylene glycol dimethacrylate, 8 g of a hydroxyethyl methacrylate and 15 g of an 11-methacryloyloxy-1,1-undecanedicarboxylic acid to prepare a homogeneous solution which was used as an adhesive.

Bovine teeth were extracted within 24 hours after slaughter, and enamel or dentin surface was ground using a #800 emery paper to be in parallel with the facial surface while pouring the water. The compressed air was blown on the ground surface for about 10 seconds to dry it, and the surface was treated with the pre-treatment agent which was the composition of the present invention for 20 seconds. Then, the treated surface was washed with the water, dried, and a double-sided tape having a hole 4 mm in diameter was adhered to the surface. Then, a paraffin with a hole which is 1.5 mm thick and 6 mm in diameter was fitted onto the above-mentioned hole in concentric therewith to imitate dental cavity. Then, the adhesive was applied thereto and was cured with light irradiation for 10 seconds by using a visible light irradiator (Witelite, produced by Takara Bermont Co.). Then, a dental composite resin (Palfique Estelite produced by Tokuyama Soda Co.) was applied thereon and was irradiated with light for 30 seconds using the visible light irradiator to prepare an adhesion test piece.

After immersed in the water at 37° C. for 24 hours, adhesive strength of the test piece was measured by using a tension tester (Autograph, produced by Shimazu Mfg. Co.) at a crosshead speed of 10 mm/min.

Adhesive strength to enamel is greatly affected by the degree of decalcification, and the adhesive strength increases with an increase in the degree of decalcification. In order to prevent the formation of a gap between the filling material and the surface of dentin, the adhesive strength to the enamel must be about 15 MPa. There does not exist any relationship between the degree of decalcification of dentin and the adhesive strength.

(2) Degree of Decalcification of Dentin

Bovine teeth were extracted within 24 hours after slaughter, and the dentin surface was ground and exposed using a #800 emery paper to be in parallel with the facial surface while pouring the water. The compressed air was blown to the surface of the dentin for about 10 seconds to dry it, and the dentin was treated with the pre-treatment agent which was the composition of the present invention and was left to stand for 20 seconds. After the surface applied with the pre-treatment agent was washed with the water, 20 dentinal tubes appearing on a screen were observed by using a scanning electron microscope (produced by Nihon Denshi Co.) in order to evaluate the degree of decalcification in terms of a ratio of the opening areas of the tubles. That is, the degree of decalcification was evaluated in six stages in which 0 was the case where the decalcification progressed up to peritubular dentin, 1 was the case where the opening degree of tubules 100 to 80%, 2 was the case where the opening degree of tubules was 80 to 60%, 3 was the case where the opening degree of tubules was 60 to 40%, 4 was the case where the opening degree of tubules was 40 to 20%, and 5 was the case where the opening degree of tubules was 20 to 0%. Usually, it is judged that dentin is favorably decalcified when the opening degree is from 40 to 0%, or from 4 to 5 in the evaluation of six stages.

Described below are abbreviations representing compounds appearing in Tables in Examples and in Comparative Examples.

PTSI-Na: sodium p-toluenesulfinic acid

PTSO-Na: sodium p-toluenesulfonic acid

PTSI-Li: lithium p-toluenesulfinic acid

DBSO-Na: sodium dodecylbenzenesulfonic acid

BSI-Na: sodium benzenesulfinic acid

BSO-Na: sodium benzenesulfonic acid
BSI-Li: lithium benzenesulfinic acid
DGME: diethylene glycol monoethyl ether
HEMA: hydroxyethyl methacrylate
HPMA: hydroxypropyl methacrylate
GMMA: glyceryl monomethacrylate
TEGDMA: triethylene glycol dimethacrylate
c-HMA: cyclohexyl methacrylate (Example 1)

1.2 Grams of maleic acid, 1.0 g of a sodium p-toluenesulfinate, 3.0 g of ethanol and 6.0 g of distilled water were mixed together to obtain a homogeneous solution thereof. 1.0 Grams of an 11-methacryloyloxy-1,1-undecanedicarboxylic acid (hereinafter referred to as MAC-

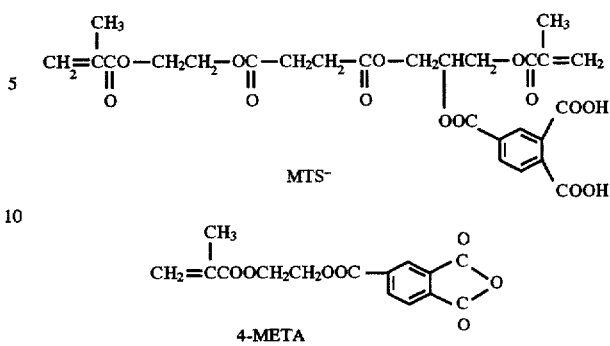

TABLE 1

| | | Acid | | Acid group-containing (meth)acrylate | | Organosulfonate/ organosulfinate | | Water-soluble organic | | Water | Hydroxy, dihydroxy (meth)acrylate | |
|---|---|---|---|---|---|---|---|---|---|---|---|---|
| | | pKa | (mmol) | monomer | (wt %) | | (wt %) | solvent | (wt %) | (%) | monomer | (wt %) |
| Example 1 | maleic acid | 1.92 | 52 | MAC-10 | 5 | PTSI-Na | 5 | ethanol | 60 | 30 | — | — |
| Example 2 | maleic acid | 1.92 | 52 | MTS | 5 | PTSO-Na | 5 | acetone ethanol | 15 10 | 65 | — | — |
| Example 3 | nitric acid | <4 | 19 | MAC-10 | 18 | PTSI-Li | 2 | ethanol | 50 | 30 | — | — |
| Example 4 | phosphoric acid | 2.15 | 110 | MAC-10 | 3 | OBSO-Na | 12 | isopropanol | 55 | 30 | — | — |
| Example 5 | tartaric acid | 3.04 | 70 | 4-META | 12 | BSI-Na | 5 | ethanol chloroform | 55 15 | 13 | — | — |
| Example 6 | citric acid | 3.16 | 80 | MAC-10 | 8 | BSO-Na | 15 | isopropanol | 37 | 40 | — | — |
| Example 7 | maleic acid | 1.92 | 60 | MAC-10 | 5 | PTSI-Na | 5 | ethanol DGME | 30 30 | 30 | — | — |
| Example 8 | maleic acid | 1.92 | 52 | MAC-10 | 5 | PTSI-Na | 5 | ethanol | 20 | 50 | HEMA | 20 |
| Example 9 | citric acid | 3.16 | 86 | MTS | 10 | BSO-Na | 15 | ethanol | 25 | 40 | HPMA | 10 |
| Example 10 | nitric acid | <4 | 20 | MAC-10 | 15 | BSI-Li | 10 | ethanol | 20 | 15 | GMMA | 40 |

10) and 9.0 g of ethanol were mixed together to obtain another homogeneous solution thereof. The two solutions were mixed together at a weight ratio of 1:1 to obtain a pre-treatment agent which was used to measure the adhesive strength to the enamel and dentin and to measure the degree of decalcification of dentin. The results were shown in Table 1. In Tables 1 and 2, the amounts of acids are in millimols per a total of 100 g of the acid group-containing (meth)acrylate monomer, organosulfonate and/or organosulfinate, water-soluble organic solvent and water.

(Examples 2 to 10)

Pre-treatment agents having compositions shown in Table 1 were prepared in accordance with the method of Example 1 in order to measure the adhesive strength to the enamel, adhesive strength to dentin and the degree of decalcification of dentin. The results were as shown in Table 2. Described below are the structures and abbreviations of the acid group-containing (meth)acrylate monomers that were used.

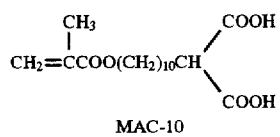

MAC-10

TABLE 2

| | Deg. of decalcification of dentin | Adhesive strength to dentin (MPa) | Adhesive strength to enamel (MPa) |
|---|---|---|---|
| Example 1 | 5 | 16.1 | 17.1 |
| Example 2 | 5 | 15.3 | 15.2 |
| Example 3 | 4 | 16.3 | 16.0 |
| Example 4 | 5 | 14.5 | 17.4 |
| Example 5 | 5 | 14.0 | 14.9 |
| Example 6 | 5 | 14.7 | 15.2 |
| Example 7 | 4 | 16.1 | 15.9 |
| Example 8 | 5 | 19.3 | 18.2 |
| Example 9 | 5 | 18.1 | 17.2 |
| Example 10 | 4 | 18.5 | 17.7 |

Examples 1, 2 and 5 represent the results with different acid group-containing (meth)acrylate monomers, and Examples 1, 3, 4, 5 and 6 represent the results with different acids. Examples 3 and 4 represent ranges of testing the amounts of acids and acid group-containing (meth)acrylate monomers. Examples 3, 6 and 9 represent ranges of testing the amounts of the organosulfonate or the organosulfinate, and Examples 2 and 5 represent ranges of testing the amounts of the water-soluble organic solvent and the water.

The pre-treatment agent of Example 5 contains a small amount of chloroform which is a water-insoluble solvent in addition to the water-soluble solvent. In all other examples, water-soluble organic solvents only are used as the organic solvents. Examples 2 and 7 are the cases where water-soluble organic solvents are mixed, and Examples 8, 9 and 10 are cases where a hydroxymethacrylate monomer is added. The above-mentioned Examples all exhibited favorable results concerning the degree of decalcification of dentin, adhesive strength to dentin and adhesive strength to enamel.

(Comparative Examples 1 to 10)

Pre-treatment agents having compositions shown in Table 3 were prepared according to the same method as that of Example 1 and were evaluated. Table 3 shows the compositions of the pre-treatment agents and Table 4 shows the results.

and adhesive strength to the tooth was defective and, particularly, adhesion strength to the dentin was poor. The pre-treatment agent of Comparative Example 5 did not contain the water. In this case, the degree of decalcification of enamel was so weak that the adhesive strength was small. In Comparative Example 6, no water-soluble organic solvent was contained, and the acid group-containing (meth)acrylate monomer did not dissolve in the water to form a heterogeneous solution. In comparative Example 7, the organic sulfonate or the organic sulfinate was not contained, and adhesive strength to dentin was poor. In Example 8, pKa of the acid was outside the range of the present invention, and adhesive strength to the dentin was poor and, particularly, adhesive strength to the enamel was poor. In Comparative Examples 9 and 10, other polymerizable monomers were contained, and adhesive strength to the tooth was poor and, particularly, adhesive strength to the dentin was poor.

TABLE 3

| | Acid | | Acid group-containing (meth)acrylate | | Organosulforate/ organosulfinate | | Water-soluble organic | | Water | Methacrylate | |
|---|---|---|---|---|---|---|---|---|---|---|---|
| | | pKa | (mmol) | monomer | (wt %) | | (wt %) | solvent | (wt %) | (%) | monomer | (wt %) |
| Comp. Example 1 | maleic acid | 1.92 | 200 | MAC-10 | 5 | PTSI-Na | 5 | ethanol | 60 | 30 | — | — |
| Comp. Example 2 | maleic acid | 1.92 | 8 | MAC-10 | 5 | PTSI-Na | 5 | ethanol | 60 | 30 | — | — |
| Comp. Example 3 | maleic acid | 1.92 | 52 | MAC-10 | 0 | PTSI-Na | 5 | ethanol | 60 | 35 | — | — |
| Comp. Example 4 | maleic acid | 1.92 | 52 | MAC-10 | 33 | PTSI-Na | 5 | ethanol | 42 | 20 | — | — |
| Comp. Example 5 | maleic acid | 1.92 | 52 | MAC-10 | 5 | PTSI-Na | 5 | ethanol | 90 | 0 | — | — |
| Comp. Example 6 | maleic acid | 1.92 | 52 | MAC-10 | 5 | PTSI-Na | 5 | — | 0 | 90 | — | — |
| Comp. Example 7 | maleic acid | 1.92 | 52 | MAC-10 | 5 | — | 0 | ethanol | 60 | 35 | — | — |
| Comp. Example 8 | acetic acid | 4.76 | 52 | MAC-10 | 5 | PTSI-Na | 5 | ethanol | 60 | 30 | — | — |
| Comp. Example 9 | maleic acid | 1.92 | 52 | MAC-10 | 5 | PTSI-Na | 5 | ethanol | 45 | 30 | TEGDMA | 15 |
| Comp. Example 10 | maleic acid | 1.92 | 52 | MAC-10 | 5 | PTSI-Na | 5 | ethanol | 50 | 30 | c-HMA | 10 |

TABLE 4

| | Deg. of decalcification of dentin | Adhesive strength to dentin (MPa) | Adhesive strength to enamel (MPa) |
|---|---|---|---|
| Comp. Example 1 | 1 | 11.1 | 19.7 |
| Comp. Example 2 | 5 | 10.3 | 10.1 |
| Comp. Example 3 | 4 | 6.5 | 15.2 |
| Comp. Example 4 | 5 | 10.1 | 13.4 |
| Comp. Example 5 | 5 | 12.7 | 8.3 |
| Comp. Example 6 | — | — | — |
| Comp. Example 7 | 4 | 7.0 | 14.8 |
| Comp. Example 8 | 5 | 10.9 | 11.2 |
| Comp. Example 9 | 5 | 9.5 | 13.1 |
| Comp. Example 10 | 5 | 10.5 | 12.9 |

In Comparative Examples 1 and 2, the acid was contained in amounts outside the range of the present invention, and the degrees of decalcification and adhesive strengths to enamel were defective. In Comparative Examples 3 and 4, the acid group-containing (meth)acrylate monomer was contained in amounts outside the range of the present invention,

We claim:

1. An agent for pre-treating a surface of a tooth prior to application of an adhesive thereto, said agent consisting essentially of an admixture of (A) (i) an inorganic acid selected from the group consisting of nitric acid, phosphoric acid, hydrochloric acid and sulfuric acid, (ii) an organic monocarboxylic acid selected from the group consisting of formic acid, lactic acid, pyruvic acid, glycolic acid, chloroacetic acid, dichloracetic acid, trichloroacetic acid and cyanoacetic acid, (iii) an organic dicarboxylic acid selected from the group consisting of tartaric acid, succinic acid, glutaric acid, maleic acid, fumaric acid, malonic acid, citraconic acid, ortho-phthalic acid, meta-phthalic acid and para-phthalic acid, or (iv) an organic tricarboxylic acid selected from the group consisting of citric acid, tricarballylic acid, 1,3,5-pentanetricarboxylic acid and trimellitic acid, (B) an acid group-containing (meth)acrylate monomer represented by the following general formula

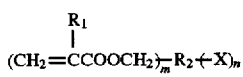

wherein $R_1$ is a hydrogen atom or a methyl group, $R_2$ is selected from the group consisting of

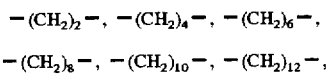

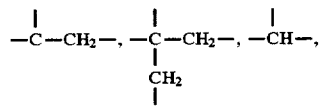

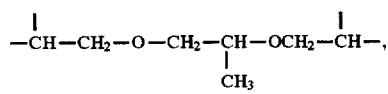

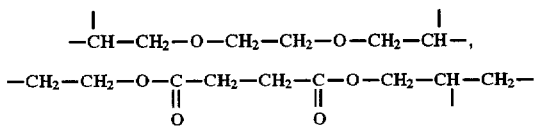

and

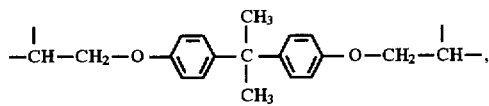

X is a group selected from the group consisting of

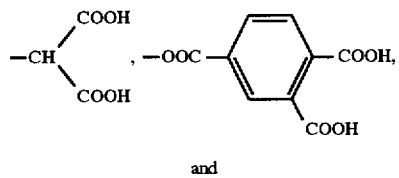

and

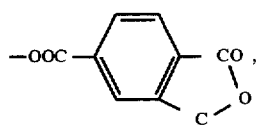

m is an integer of 1 to 4, and n is an integer of 1 or 2, (C) an organosulfonate and/or an organosulfinate, (D) a water-soluble organic solvent, and (E) water;

wherein the acid (A) is present in an amount of from 15 to 150 mmols based on a total of 100 g of (B), (C), (D) and (E); the monomer (B) being present in an amount of from 1 to 30 parts by weight based on a total of 100 parts by weight of (B), (C), (D) and (E); the organosulfonate and/or the organosulfinate (C) being present in an amount of from 1 to 20 parts by weight based on a total of 100 parts by weight of (B), (C), (D) and (E); the solvent (D) being present in an amount of from 10 to 90 parts by weight based on a total of 100 parts by weight of (B), (C), (D) and (E); and the water (E) being present in an amount of from 5 to 80 parts by weight based on a total of 100 parts by weight of (B), (C), (D) and (E).

2. An agent for pre-treating a surface of a tooth prior to application of an adhesive thereto, said agent consisting essentially of an admixture of (A) (i) an inorganic acid selected from the group consisting of nitric acid, phosphoric acid, hydrochloric acid and sulfuric acid, (ii) an organic monocarboxylic acid selected from the group consisting of formic acid, lactic acid, pyruvic acid, glycolic acid, chloroacetic acid, dichloracetic acid, trichloroacetic acid and cyanoacetic acid, (iii) an organic dicarboxylic acid selected from the group consisting of tartaric acid, succinic acid, glutaric acid, maleic acid, fumaric acid, malonic acid, citraconic acid, ortho-phthalic acid, meta-phthalic acid and para-phthalic acid, or (iv) an organic tricarboxylic acid selected from the group consisting of citric acid, tricarballylic acid, 1,3,5-pentanetricarboxylic acid and trimellitic acid, (B) an acid group-containing (meth)acrylate monomer represented by the following general formula

wherein $R_1$ is a hydrogen atom or a methyl group, $R_2$ is selected from the group consisting of

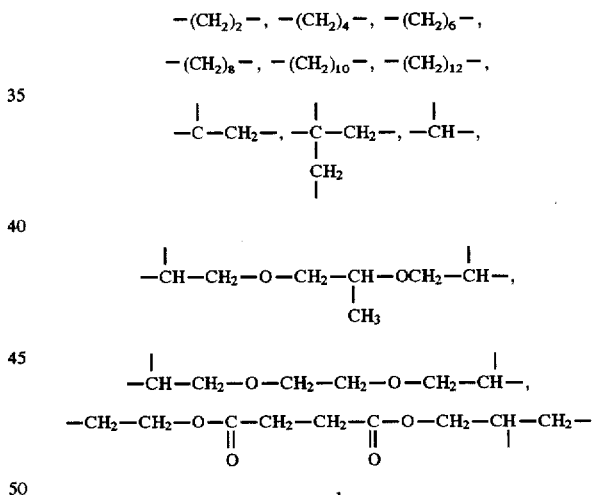

and

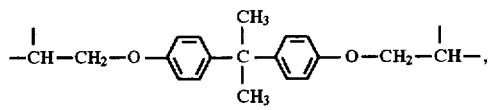

X is a group selected from the group consisting of

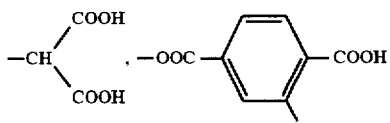

and

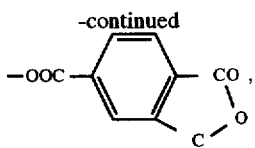

m is an integer of 1 to 4, and n is an integer of 1 or 2.

(C) an organosulfonate and/or an organosulfinate, (D) a water-soluble organic solvent, (E) water, and (F) a hydroxy- or a dihydroxy (meth)acrylate monomer; wherein the acid (A) is present in an amount of from 15 to 150 mmol based on a total of 100 g of (B), (C), (D), (E) and (F); the monomer (B) being present in an amount of from 1 to 30 parts by weight based on a total of 100 parts by weight of (B), (C), (D), (E) and (F); the organosulfonate and/or the organo-sulfinate (C) being present in an amount of from 1 to 20 parts by weight based on a total of 100 parts by weight of (B), (C), (D), (E) and (F); the solvent (D) being present in an amount of from 10 to 90 parts by weight based on a total of 100 parts by weight of (B), (C), (D), (E) and (F); the water (E) being present in an amount of from 5 to 80 parts by weight based on a total of 100 parts by weight of (B), (C), (D), (E) and (F); and the monomer (F) being present in an amount of from 1 to 40 parts by weight based on a total of 100 parts by weight of (B), (C), (D), (E) and (F).

3. The agent according to claim 1 or 2, wherein the organosulfinate (C) is a metal salt of an aromatic alkali sulfinate.

4. The agent according to claim 1 or 2, wherein the water-soluble organic solvent (D) is an alcohol.

5. The agent according to claim 2, wherein the hydroxy- or dihydroxyalkyl(meth)acrylate monomer is a monoester of a polyhydric alcohol having not more than 3 carbon atoms and a (meth)acrylic acid.

6. The agent according to claim 1, wherein said composition does not contain a polymerizable (meth)acrylate monomer other than an acid group-containing (meth)acrylate monomer (B).

* * * * *